United States Patent [19]

Wells et al.

[11] Patent Number: 4,501,889

[45] Date of Patent: * Feb. 26, 1985

[54] MORPHOLINE COMPOUNDS PREPARED VIA PHOSPHATE CATALYSTS

[75] Inventors: James E. Wells, Ardmore; Victoria Eskinazi, Boothwyn, both of Pa.

[73] Assignee: Air Products and Chemicals, Inc., Allentown, Pa.

[*] Notice: The portion of the term of this patent subsequent to May 1, 2001 has been disclaimed.

[21] Appl. No.: 381,233

[22] Filed: May 24, 1982

[51] Int. Cl.³ .......................................... C07D 295/02
[52] U.S. Cl. .................................................. 544/106
[58] Field of Search ........................................ 544/106

[56] References Cited

U.S. PATENT DOCUMENTS 3,151,112  9/1964  Moss ................................... 544/106

*Primary Examiner*—Robert W. Ramsuer
*Attorney, Agent, or Firm*—Russell L. Brewer; Richard A. Dannells, Jr.; E. Eugene Innis

[57] ABSTRACT

Certain hydrogen phosphate and pyrophosphate compositions are employed as catalysts for organic condensation reactions. Specifically, a diethylene glycolamine compound is converted to a morpholine compound in the presence of such a catalyst.

6 Claims, No Drawings

MORPHOLINE COMPOUNDS PREPARED VIA PHOSPHATE CATALYSTS

TECHNICAL FIELD OF THE INVENTION

The present invention relates to organic condensation reactions effected in the presence of novel pyrophosphate and hydrogen phosphate catalysts and is more particularly concerned with the production of morpholine compounds in enhanced yields.

BACKGROUND OF THE PRIOR ART

Organic synthesis by condensation reactions resulting in the loss of a molecule of water or of ammonia are well known in the art. Certain of such reactions are generally effected in the presence of acidic catalysts. An important area in which such acid catalysis has been employed is in cyclization reactions as in the synthesis of triethylenediamine and its C-substituted homologues. The catalysts more generally used or proposed for use in such cyclization reactions are solid products of the Lewis acid type.

Triethylenediamine, also called diazabicyclo-[2.2.2]-octane, has been widely employed commercially as a catalyst in organic isocyanate reactions with compounds containing labile hydrogen, as in the production of urethane polymers. Triethylenediamine (sometimes hereinafter referred to as TEDA) was initially prepared in significant quantities by methods such as that described in U.S. Pat. No. 2,937,176, by passing aliphatic amines in vapor phase over acidic cracking catalyst, such as silica-alumina dried gel or acid-activated clays. Numerous other feed stocks as well as other catalysts are disclosed in subsequent patents for preparation of TEDA as well as C-alkyl derivatives thereof.

Typical among these are U.S. Pat. Nos. 2,985,658 and 3,166,558 employing preferably silica-alumina type catalyst, but listing also other useful solid acid catalysts that can be employed such as alumina in which phosphate or fluoride ion is incorporated (U.S. Pat. No. 2,985,658).

Among other catalysts proposed in the patent art for preparation of triethylene diamine and/or C-alkyl homologues thereof, are certain phosphate compounds, particularly aluminum phosphate.

The use of aluminum phosphate as a catalyst in the preparation of heterocyclic compounds from aliphatic amines was early disclosed in U.S. Pat. No. 2,467,205, particularly for the preparation of piperazine from ethylenediamine or from polyethylene polyamine. The use of aluminum phosphate as catalyst in the preparation of triethylenediamine accompanied by piperazine among other by-products is further described in U.S. Pat. No. 3,172,891; while U.S. Pat. No. 3,342,820 describes the use of complex phosphates of alkali metal and trivalent metals in the preparation of C-alkyl TEDA.

U.S. Pat. No. 3,297,701 discloses as catalysts for preparation of TEDA and C-alkyl TEDA, in addition to the preferred aluminum phosphate stated to be superior, other phosphate compounds including calcium and iron phosphates among other listed metal phosphates. In the conversion of N-aminoethylpiperazine to triethyleneadiamine over aluminum phosphate catalyst, at most up to 39 mol% triethylenediamine is said to be obtained. Other of the named metal phosphate catalysts in the examples of the patent obtain yields of less than 10 mol% TEDA.

Acid metal phosphate catalysts, particularly phosphates of boron, aluminum and trivalent iron, have also been proposed for use in intramolecular cyclic dehydration reactions and other condensation reactions involving amino compounds. Examples of such reactions are found in U.S. Pat. No. 4,117,227, which discloses conversion of an N-substituted diethanolamine to the corresponding N-substituted morpholine. U.S. Pat. No. 4,036,881 describes preparation of non-cyclic polyalkylene polyamines by condensation of an alkylene diamine with an ethanolamine. N-hydroxethylmorpholine is condensed with morpholine in the presence of aluminum phosphate catalyst to form dimorpholino ethane according to U.S. Pat. No. 4,103,087. Similarly, dimorpholinodiethyl ether is obtained by condensation of hydroxyethyl morpholine with aminoethyl morpholine over iron, aluminum or boron phosphate in U.S. Pat. No. 4,095,022. Reaction of piperazine with ethanolamine over such acidic metal phosphate produces N-aminoethyl piperazine according to U.S. Pat. No. 4,049,657. U.K. Pat. No. 1,492,359 discloses the preparation of morpholine compounds by reacting an aminoalkoxyalkanol compound over phosphoric acid and similar types of phosphorus-containing substances.

Pyrophosphates of lithium, sodium, strontium and barium have been used as dehydration catalysts; see U.S. Pat. No. 3,957,900. Phosphates and pyrophosphates of strontium and nickel have been used for the dehydrogenation of, for example, n-butene to butadiene under the conditions described in U.S. Pat. No. 3,541,172.

SUMMARY OF THE INVENTION

It has now been found that high yields of morpholine compounds, e.g. morpholine and alkyl morpholine wherein the alkyl group has from 1 to 6 carbon atoms, are selectively obtained from Diglycolamine (registered trademark for 2-(2-aminoethoxy)ethanol, also known as diethylene glycolamine) compounds, e.g. Diglycolamine and substituted Diglycolamines, when the synthesis thereof is carried out in the presence of catalytic amounts of a catalyst selected from the group consisting of the pyrophosphate, monohydrogen phosphate and dihydrogen phosphate of strontium, copper, magnesium, calcium, barium, zinc, aluminum, lanthanum, cobalt, nickel, cerium and neodymium and mixtures thereof.

In contrast to the morpholine synthesis methods of the prior art, high yields of morpholine compounds are selectively obtained at low pressures, i.e. less than 2 atmospheres, and low temperatures without the use of hydrogen.

DETAILED DESCRIPTION OF THE INVENTION

The monohydrogen and dihydrogen phosphate catalysts of the present invention are prepared by reaction of a mono- or diphosphate of an alkali metal or ammonium with a soluble salt of strontium, copper, magnesium, calcium, barium, zinc, aluminum, lanthanum, cobalt, nickel, cerium or neodymium at ambient temperatures. The highest purity and best yields of the present invention are obtained when using the soluble metal salts of a strong acid such as the metal nitrates, in substantially stoichiometric proportion to the phosphate. In aqueous media under these conditions, the reaction mixture is at a pH of about 3.5 to 6.5. In general, to obtain a precipitate of desired high content of the metal monohydrogen or dihydrogen phosphate, the ratio of phosphate to metal salt in the reaction mixture should be such as to have a pH of 5±3, or the mixture should be adjusted to that pH range.

The pyrophosphate form of the catalysts of the present invention are prepared by heat treating the metal monohydrogen or dihydrogen phosphate product at temperatures above about 300° C. up to 750° C. in the presence of a mixture of steam and air, preferably at least about 20% by volume of steam.

For use as a catalyst, the metal pryo-, monohydrogen or dihydrogen phosphate product may be employed in the form of irregular particles of the desired size range prepared by breaking up the washed and dried filter cake or in the form of regular shaped pellets obtained by known methods of casting or extruding or the product may be deposited or otherwise impregnated into the pores of a microporous substrate such as a silica-alumina. In using the catalyst of the present invention to catalyze organic condensation reactions, substantially the same conditions may be employed as when using the known catalysts for the particular synthesis. For optimum results, however, some adjustment in temperature, diluent and/or space rate may be found beneficial. In the production of morpholine the temperature is in the range of about 285° to 420° C., the pressure in the range of about 0.1 to 1.5 atmospheres, the liquid hourly space velocity (LHSV) of the organic feed stock per volume of catalyst is in the range of about 0.05 to 1.5. Preferably, the temperature is in the range of about 300° to 370° C., the pressure is in the range of about 0.3 to 1.0 atmospheres and the LHSV is in the range of about 0.1 to 0.3 to obtain the highest yields and most economical process. The operable ratio of the organic feeds to water diluent is about 10 to 90% on a weight basis and preferably, 60–80% by weight. The optimum yield of morpholine is likely to be obtained using the highest temperature in the preferred range at the LHSV. The yield of morpholine can also be improved with any of the catalysts of the present invention by carrying out the condensation reaction in the presence of an inert diluent gas such as nitrogen, argon, helium and the like in ratios of 2:1 to 10:1 inert gas to liquid organic feed stock.

The organic feedstock used in this reaction is Diglycolamine (DGA) and alkyl-substituted DGA wherein the alkyl group has from 1 to 6 carbon atoms.

EXAMPLE 1

200 grams of strontium nitrate [$Sr(NO_3)_2$] was dissolved in distilled water and brought to a total volume of 800 cc with distilled water. To this solution there was added 10 cc of 85% phosphoric acid followed by 34.5 cc of 50% sodium hydroxide added rapidly with vigorous stirring. The resultant fine white precipitate was stirred for 10 minutes, vacuum-filtered and water-washed. The obtained filter cake was air dried in a static oven at approximately 110° C. and extruded into ⅛ inch pellets for evaluation.

The obtained product had a surface area of 10–15 $m^2/g$. By X-ray diffraction the principal component was identified as $\beta$-$SrHPO_4$ with minor quantities of $Sr_5(OH)(PO_4)_3$ and unreacted $Sr(NO_3)_2$. Infrared spectroscopy showed a spectrum consistent with $SrHPO_4$. (Ref: Richard A. Nygurst and Ronald O. Kagel, "Infrared spectra of Inorganic Compounds", page 163, 1971).

EXAMPLES 2–6

The product of Example 1 was evaluated for catalytic performance for the preparation of morpholine from Diglycolamine at 1 atmosphere in accordance with the following test procedure:

(a) 10 cc (approximately 3.1 g.) of $SrHPO_4$ was loaded into a ¾" diameter stainless steel reactor.

(b) The reactor was placed in a conventional tube furnace such that the catalyst bed was near the furnace center and therefore could be heated to a constant and uniform temperature.

(c) The catalyst bed temperature was slowly raised to a temperature of 250° C. over a period of 15 to 30 minutes while a small flow of gaseous helium was maintained through the reactor in three of the examples.

(d) A feed mixture containing DGA and water (except for Example (6) in the ratio set forth in Table 1 below was then allowed to flow through the catalyst bed at an LHSV of 0.21 to 0.88; the helium flow was continued through the run (except for Examples 5–6).

(e) The catalyst bed temperature indicated in the tables set forth below were maintained throughout the run and the product samples were collected and analyzed. Analyses were performed using well-established gas chromatographic techniques.

The operating conditions and yields obtained from the catalyst of Examples 1 are summarized in Table 1 below.

TABLE 1

| Example | 2 | 3 | 4 | 5 | 6 |
| --- | --- | --- | --- | --- | --- |
| Feed, DGA/H₂O, Vol. % | 80/20 | 100/0 | 80/20 | 100/0 | 50/50 |
| Helium Diluent, cc/min. | 34.5 | 34 | 28.5 | None | None |
| Temp., °C. | 320 | 320 | 370 | 350 | 330 |
| Contact Time, sec. | 12 | 55 | 12 | 13 | 22 |
| LHSV | 0.21 | 0.21 | 0.44 | 0.88 | 0.21 |
| Yield of Morpholine, mol. % | 85 | 63 | 37 | 46 | 75 |
| Selectivity to Morpholine % | 85 | 74 | 37 | 57.5 | 75.6 |
| Conv. of DGA mol. % | 100 | 85 | 100 | 80 | 99 |
| Dioxane Yield, mol. % | ← | ← | less than 1% | → | → |

In each of the Examples 2–6, it was unexpectedly found that DGA could be to selectively converted to morpholine without the conversion of appreciable quantities of dioxane, tar or other high molecular weight components. It would be expected that the reaction product from DGA conversion would contain substantially equal amounts of dioxane and morpholine.

EXAMPLES 7–33

The test procedure set forth in Examples 2–6 was followed in Examples 7–33 in the presence of the Example 1 catalyst. Table 2 below sets forth the feed mixture, operating conditions and the product yields for each example.

TABLE 2

| Example | DGA/H₂O, Vol. % | Temp. °C. | LHSV | Helium Diluent, cc/min. | Conversion of DGA, mol. % | Morpholine yield, mol. % | Morpholine % Selectivity |
|---|---|---|---|---|---|---|---|
| 7 | 100/0 | 370° C. | 0.44 | None | 99 | 36 | 36 |
| 8 | 100/0 | 370° C. | 0.88 | None | 99 | 47 | 47 |
| 9 | 100/0 | 370° C. | 1.3 | None | 94 | 48 | 51 |
| 10 | 100/0 | 350° C. | 0.44 | None | 93 | 47 | 51 |
| 11 | 100/0 | 340° C. | 0.21 | None | 95 | 51 | 54 |
| 12 | 100/0 | 330° C. | 0.21 | None | 100 | 53 | 53 |
| 13 | 100/0 | 320° C. | 0.88 | None | 83 | 43 | 52 |
| 14 | 80/20 | 370° C. | 0.44 | None | 100 | 43 | 43 |
| 15 | 80/20 | 350° C. | 0.44 | None | 93 | 57 | 61 |
| 16 | 80/20 | 350° C. | 0.44 | 28.5 | 100 | 55 | 55 |
| 17 | 80/20 | 340° C. | 0.67 | 28.5 | 93 | 49 | 53 |
| 18 | 80/20 | 330° C. | 0.44 | 28.5 | 95 | 57 | 60 |
| 19 | 80/20 | 330° C. | 0.31 | 28.4 | 100 | 68 | 68 |
| 20 | 80/20 | 325° C. | 0.21 | None | 94 | 47 | 50 |
| 21 | 80/20 | 320° C. | 0.31 | 28.5 | 95 | 73 | 77 |
| 22 | 80/20 | 320° C. | 0.21 | 28.5 | 100 | 81 | 81 |
| 23 | 80/20 | 320° C. | 0.44 | 28.5 | 90 | 46 | 51 |
| 24 | 80/20 | 320° C. | 0.14 | 28.5 | 100 | 73 | 73 |
| 25 | 80/20 | 320° C. | 0.67 | None | 79 | 30 | 38 |
| 26 | 80/20 | 320° C. | 0.31 | None | 86 | 35 | 41 |
| 27 | 80/20 | 310° C. | 0.44 | 28.5 | 82 | 38 | 46 |
| 28 | 50/50 | 320° C. | 0.31 | None | 77 | 46 | 60 |
| 29 | 50/50 | 320° C. | 0.21 | None | 97 | 72 | 74 |
| 30 | 65/35 | 320° C. | 0.21 | None | 98 | 54 | 55 |
| 31 | 65/35 | 330° C. | 0.31 | None | 79 | 50 | 63 |
| 32 | 35/65 | 325° C. | 0.31 | None | 73 | 54 | 74 |
| 33 | 35/65 | 325° C. | 0.21 | None | 100 | 60 | 60 |

What is claimed is:

1. A process which comprises converting a diglycolamine compound to a morpholine compound at a temperature in the range of about 285° C. to 420° C., and in the presence of a catalyst selected from the group consisting of the pyrophosphate and the monohydrogen and dihydrogen phosphate of strontium.

2. The method as defined in claim 1 wherein said catalyst is associated with a carrier of the group consisting of silica, alumina and silica-alumina.

3. The process of claim 1 wherein said catalyst is the monohydrogen phosphate or dihydrogen phosphate of strontium or mixtures thereof.

4. The process of claims 1 or 2 wherein the conversion takes place in the presence of water.

5. The process of claims 1 or 2 wherein the conversion takes place in the presence of an inert gas.

6. The process of claim 1 wherein said diglycolamine compound is selected from the group consisting of diethylene glycolamine and alkyl diethylene glycolamine and mixtures thereof and said morpholine compound is selected from the group consisting of morpholine and alkyl morpholine and mixtures thereof, wherein each of said alkyl groups contains from 1 to 6 carbon atoms.

* * * * *